United States Patent
Taurino et al.

(10) Patent No.: US 11,937,632 B2
(45) Date of Patent: Mar. 26, 2024

(54) CARTRIDGE FOR AN AEROSOL-GENERATING SYSTEM

(71) Applicant: PHILIP MORRIS PRODUCTS S.A., Neuchatel (CH)

(72) Inventors: Irene Taurino, Lausanne (CH); Igor Zinovik, Peseux (CH)

(73) Assignee: Philip Morris Products S.A., Neuchatel (CH)

( * ) Notice: Subject to any disclaimer, the term of this patent is extended or adjusted under 35 U.S.C. 154(b) by 636 days.

(21) Appl. No.: 16/973,826

(22) PCT Filed: Jun. 28, 2019

(86) PCT No.: PCT/EP2019/067465
§ 371 (c)(1),
(2) Date: Dec. 10, 2020

(87) PCT Pub. No.: WO2020/002671
PCT Pub. Date: Jan. 2, 2020

(65) Prior Publication Data
US 2021/0244091 A1    Aug. 12, 2021

(30) Foreign Application Priority Data

Jun. 29, 2018 (EP) .................... 18180841

(51) Int. Cl.
*A24F 40/30* (2020.01)
*A24F 40/10* (2020.01)
(Continued)

(52) U.S. Cl.
CPC .............. *A24F 40/30* (2020.01); *A24F 40/10* (2020.01); *A24F 40/42* (2020.01); *A24F 40/44* (2020.01);
(Continued)

(58) Field of Classification Search
None
See application file for complete search history.

(56) References Cited

U.S. PATENT DOCUMENTS

| 4,765,348 A | 8/1988 | Honeycutt |
|---|---|---|
| 10,645,973 B2 | 5/2020 | Silvestrini |

(Continued)

FOREIGN PATENT DOCUMENTS

| JP | 2018-502587 | 2/2018 |
|---|---|---|
| JP | 2018-504127 | 2/2018 |

(Continued)

OTHER PUBLICATIONS

Search Report and Written Opinion for PCT/EP2019/067465 dated Sep. 30, 2019 (12 pages).

(Continued)

*Primary Examiner* — James Harvey
(74) *Attorney, Agent, or Firm* — Mueting Raasch Group

(57) ABSTRACT

There is provided a cartridge (100) for use in an aerosol-generating system (10) for the generation of an aerosol comprising nicotine salt particles. The cartridge (100) comprises a first compartment (110) containing a nicotine source (210) comprising a first carrier material (211) impregnated with nicotine, the first compartment (110) having a first air inlet (132) and a first air outlet (133). The first compartment (110) defines a first airflow path (217) extending across a first surface (213) of the first carrier material (211) between the first air inlet (132) and the first air outlet (133). The cartridge (100) also comprises a second compartment (120) containing an acid source (220) comprising a second carrier material (221) impregnated with an acid, the second compartment (220) having a second air inlet (134) and a second air outlet (135). The second compartment (220) defines a second airflow path (227) extending across a first surface (223) of the second carrier material (221) between the (Continued)

second air inlet (134) and the second air outlet (135). The first compartment (110) and the second compartment (220) are arranged in parallel within the cartridge (100). A thickness of at least one of the first carrier material (211) and the second carrier material (221) varies in a direction along the first airflow path (217) or the second airflow path (227) respectively.

15 Claims, 5 Drawing Sheets

(51) Int. Cl.
    *A24F 40/42*         (2020.01)
    *A24F 40/44*         (2020.01)
    *A24F 40/465*       (2020.01)
    *A24F 40/48*         (2020.01)
    *A61M 11/04*        (2006.01)

(52) U.S. Cl.
    CPC ............ *A24F 40/465* (2020.01); *A24F 40/48* (2020.01); *A61M 11/042* (2014.02)

(56) References Cited

U.S. PATENT DOCUMENTS

| | | |
|---|---|---|
| 10,834,968 B2 | 11/2020 | Edward |
| 2021/0212368 A1* | 7/2021 | Taurino ................. A61M 15/06 |
| 2021/0244091 A1* | 8/2021 | Taurino ................... A24F 40/48 |
| 2023/0000131 A1* | 1/2023 | Spadaro .................. A24F 40/42 |
| 2023/0023830 A1* | 1/2023 | Taurino ................ A24B 15/167 |

FOREIGN PATENT DOCUMENTS

| | | |
|---|---|---|
| WO | WO 2014/140230 | 9/2014 |
| WO | WO 2014/140320 | 9/2014 |
| WO | WO 2014/187763 | 11/2014 |
| WO | WO 2015/000974 | 1/2015 |
| WO | WO 2016/107763 | 7/2016 |
| WO | WO 2017/029268 | 2/2017 |
| WO | WO 2017/068099 | 4/2017 |
| WO | WO 2017/108983 | 6/2017 |
| WO | WO 2017/108987 | 6/2017 |
| WO | WO 2017/211600 | 12/2017 |
| WO | WO 2018/020039 | 2/2018 |
| WO | WO 2018/099999 | 6/2018 |
| WO | WO 2019/234245 | 12/2019 |
| WO | WO 2019/243612 | 12/2019 |
| WO | WO 2020/020647 | 1/2020 |
| WO | WO 2020/020916 | 1/2020 |
| WO | WO 2020/020917 | 1/2020 |

OTHER PUBLICATIONS http://www.sodim.com/en/nc/products/physical-testing/detail/product/smi-pressure-drop.html#Overview (2 pages), last visited Mar. 2, 2021.

Office Action issued in Japan for Application No. 2020-568770 dated Jun. 19, 2023 (9 pages). English translation included.

* cited by examiner

CARTRIDGE FOR AN AEROSOL-GENERATING SYSTEM

This application is a U.S. National Stage Application of International Application No. PCT/EP2019/067465 filed Jun. 28, 2019, which was published in English on Jan. 2, 2020 as International Publication No. WO 2020/002671 A1. International Application No. PCT/EP2019/067465 claims priority to European Application No. 18180841.1 filed Jun. 29, 2018.

The present invention relates to a cartridge for use in an aerosol-generating system, the cartridge comprising at least one carrier material having a varying thickness. The present invention also relates to an aerosol-generating system comprising the cartridge.

In some handheld aerosol-generating systems, an electrical heater is used for heating a nicotine source and a volatile delivery enhancing compound, for example an acid source. In these aerosol-generating devices, vaporised nicotine and acid react with each other in the gas phase to form an aerosol of nicotine salt particles that is inhaled by a user.

Differences between the vapour concentrations of nicotine and the acid in such systems may disadvantageously lead to an unfavourable reaction stoichiometry or the delivery of excess reactant, such as unreacted nicotine vapour or unreacted acid vapour to a user. Consequently, it is known to control and balance the concentration of acid vapour and nicotine vapour to yield an efficient reaction stoichiometry through differential heating of the nicotine source and the acid source.

For example, WO 2014/140230 A1 discloses controlling the formation of an aerosol of nicotine salt particles by an aerosol-generating system comprising an aerosol-generating article comprising a first compartment comprising an acid source and a second compartment comprising a nicotine source by heating the first compartment to a temperature lower than the second compartment.

It is also known to control and balance the concentration of acid vapour and nicotine vapour to yield an efficient reaction stoichiometry through variation of the volumetric airflow through the compartments containing the nicotine source and the acid source. For example, WO 2017/108987 A1 teaches that the ratio of nicotine and lactic acid required to achieve an appropriate reaction stoichiometry may be controlled and balanced through variation of the volumetric airflow through a first compartment of a cartridge relative to the volumetric airflow through a second compartment of a cartridge. WO 2017/108987 A1 teaches that the ratio of the volumetric airflow through the first compartment relative to the volumetric airflow through the second compartment may be controlled through variation of the flow area of a first air inlet of the first compartment of the cartridge relative to the flow area of a second air inlet of the second compartment of the cartridge.

However, the present inventors have recognised that other factors may act to drive the relative amounts of nicotine vapour and acid vapour away from an efficient reaction stoichiometry. For example, known systems typically comprise a first compartment containing a nicotine source comprising a first planar carrier material impregnated with nicotine and a second compartment containing an acid source comprising a second planar carrier material impregnated with an acid. The present inventors have found that uniform variations in the dimensions of the first and second carrier materials, which may arise for example due to manufacturing tolerances, may affect the resistance to draw of the first and second compartments, which may undesirably alter the volumetric airflow through the first and second compartments. Inconsistent volumetric airflow through the first and second compartments due to manufacturing tolerances may adversely affect the ratio of nicotine vapor to acid vapor. Inconsistent volumetric airflow through the first and second compartments due to manufacturing tolerances may result in an inconsistent user experience across the use of a plurality of cartridges.

It would be desirable to provide a cartridge for an aerosol-generating system for the generation of an aerosol comprising nicotine salt particles, wherein the cartridge reduces or mitigates the effect of manufacturing tolerances in the dimensions of a carrier material.

According to a first aspect of the present invention there is provided a cartridge for use in an aerosol-generating system for the generation of an aerosol comprising nicotine salt particles. The cartridge comprises a first compartment containing a nicotine source comprising a first carrier material impregnated with nicotine, the first compartment having a first air inlet and a first air outlet. The first compartment defines a first airflow path extending across a first surface of the first carrier material between the first air inlet and the first air outlet. The cartridge also comprises a second compartment containing an acid source comprising a second carrier material impregnated with an acid, the second compartment having a second air inlet and a second air outlet. The second compartment defines a second airflow path extending across a first surface of the second carrier material between the second air inlet and the second air outlet. The first compartment and the second compartment are arranged in parallel within the cartridge. A thickness of at least one of the first carrier material and the second carrier material varies in a direction along the first airflow path or the second airflow path respectively.

As used herein with reference to the invention, the term "air inlet" is used to describe one or more apertures through which air may be drawn into a component or portion of a component of the cartridge.

As used herein with reference to the invention, the term "air outlet" is used to describe one or more apertures through which air may be drawn out of a component or portion of a component of the cartridge.

As used herein with reference to the first and second compartments, by "parallel" it is meant that the first compartment and the second compartment are arranged within the cartridge so that in use a first air stream drawn through the cartridge passes into the first compartment through the first air inlet, downstream through the first compartment and out of the first compartment through the first air outlet and a second air stream drawn through the cartridge passes into the second compartment through the second air inlet, downstream through the second compartment and out of the second compartment through the second air outlet. Nicotine vapour is released from the nicotine source in the first compartment into the first air stream drawn through the cartridge and acid vapour is released from the acid source in the second compartment into the second air stream drawn through the cartridge. The nicotine vapour in the first air stream reacts with the acid vapour in the second air stream in the gas phase to form an aerosol of nicotine salt particles.

Cartridges according to the present invention comprise first and second carrier materials, wherein a thickness of at least one of the first and second carrier materials varies in a direction along the first airflow path or the second airflow path respectively.

Advantageously, the present inventors have recognised that using a carrier material having a varying thickness along an airflow path across a surface of the carrier material reduces or mitigates the effect of manufacturing tolerances in the thickness of the carrier material when compared to known systems comprising a carrier material having a uniform planar shape. In other words, uniform variance in the thickness of a carrier material due to manufacturing tolerances has a reduced or mitigated effect on volumetric airflow through the compartment containing the carrier material when the carrier material is formed with a varying thickness along the length of an airflow path across a surface of the carrier material.

Advantageously, the present inventors have recognised that using a carrier material having a varying thickness along an airflow path across a surface of the carrier material facilitates more precise control of the resistance to draw through the compartment containing the carrier material. Advantageously, more precise control of the resistance to draw through at least one of the first and second compartments facilitates control of the ratio of nicotine vapor and acid vapor, which facilitates an efficient reaction stoichiometry.

Preferably, a thickness of the first carrier material varies in a direction along the first airflow path and a thickness of the second carrier material varies in a direction along the second airflow path. Advantageously, providing each of the first and second carrier materials with a varying thickness along the length of the respective airflow path may reduce or mitigate the effect of manufacturing tolerances in the thickness of the carrier materials on the volumetric airflow through both of the first and second compartments.

In embodiments in which the first carrier material has a varying thickness along the length of the first airflow path, the first carrier material may have a tapered shaped.

In embodiments in which the first carrier material has a varying thickness along the length of the first airflow path, preferably at least a portion of the first surface of the first carrier material has a non-planar shape. Advantageously, a non-planar first surface of the first carrier material may optimise the reduction or mitigation of the effect of manufacturing tolerances in the thickness of the first carrier material. At least a portion of the first surface of the first carrier material may have at least one of a convex shape, a concave shape, an undulating shape, a multifaceted shape, one or more depressions, and one or more protrusions. The first surface of the first carrier material may have a symmetrical shape. The first surface of the first carrier material may have an asymmetrical shape.

In embodiments in which at least a portion of the first surface of the first carrier material has one or more protrusions, the one or more protrusions may have any suitable size and shape.

The one or more protrusions may each have a cuboid shape. The one or more protrusions may each have a domed shape. The one or more protrusions may each have a hemispherical shape. The one or more protrusions may be arranged in a grid or an array over at least a portion of the first surface of the first carrier material.

The one or more protrusions may comprise one or more elongate ridges. Preferably, the one or more elongate ridges extend perpendicularly with respect to the first airflow path.

In embodiments in which at least a portion of the first surface of the first carrier material has one or more depressions, the one or more depressions may have any suitable size and shape.

The one or more depressions may each have a cuboid shape. The one or more depressions may each have a bowl shape. The one or more depressions may each have a hemispherical shape. The one or more depressions may be arranged in a grid or an array over at least a portion of the first surface of the first carrier material.

The one or more depressions may comprise one or more elongate grooves. Preferably, the one or more elongate grooves extend perpendicularly with respect to the first airflow path.

In embodiments in which at least a portion of the first surface of the first carrier material has a multifaceted shape, the multifaceted shape may comprise at least one of an inclined portion and a declined portion. As used herein, an "inclined portion" is a portion of the carrier material exhibiting a linear increase in thickness of the carrier material in the direction of airflow along the airflow path across the first surface. As used herein, a "declined portion" is a portion of the carrier material exhibiting a linear decrease in thickness of the carrier material in the direction of airflow along the airflow path across the first surface.

In embodiments in which the second carrier material has a varying thickness along the length of the second airflow path, the second carrier material may have a tapered shaped.

In embodiments in which the second carrier material has a varying thickness along the length of the second airflow path, preferably at least a portion of the first surface of the second carrier material has a non-planar shape. Advantageously, a non-planar first surface of the second carrier material may optimise the reduction or mitigation of the effect of manufacturing tolerances in the thickness of the second carrier material. At least a portion of the first surface of the second carrier material may have at least one of a convex shape, a concave shape, an undulating shape, a multifaceted shape, one or more depressions, and one or more protrusions. The first surface of the second carrier material may have a symmetrical shape. The first surface of the second carrier material may have an asymmetrical shape.

In embodiments in which at least a portion of the first surface of the second carrier material has one or more protrusions, the one or more protrusions may have any suitable size and shape.

The one or more protrusions may each have a cuboid shape. The one or more protrusions may each have a domed shape. The one or more protrusions may each have a hemispherical shape. The one or more protrusions may be arranged in a grid or an array over at least a portion of the first surface of the second carrier material.

The one or more protrusions may comprise one or more elongate ridges. Preferably, the one or more elongate ridges extend perpendicularly with respect to the second airflow path.

In embodiments in which at least a portion of the first surface of the second carrier material has one or more depressions, the one or more depressions may have any suitable size and shape.

The one or more depressions may each have a cuboid shape. The one or more depressions may each have a bowl shape. The one or more depressions may each have a hemispherical shape. The one or more depressions may be arranged in a grid or an array over at least a portion of the first surface of the second carrier material.

The one or more depressions may comprise one or more elongate grooves. Preferably, the one or more elongate grooves extend perpendicularly with respect to the second airflow path.

In embodiments in which at least a portion of the first surface of the first carrier material has a multifaceted shape, the multifaceted shape may comprise at least one of an inclined portion and a declined portion.

Preferably, the cartridge comprises a cartridge housing defining the first compartment and the second compartment. Preferably, the first carrier material is secured to the cartridge housing at a second surface of the first carrier material and the second carrier material is secured to the cartridge housing at a second surface of the second carrier material.

Preferably, the first surface of the first carrier material is opposite the second surface of the first carrier material. In other words, preferably the first and second surfaces define opposite sides of the first carrier material. The thickness of the first carrier material extends between the first and second surfaces of the first carrier material.

Preferably, the first surface of the second carrier material is opposite the second surface of the second carrier material. In other words, preferably the first and second surfaces define opposite sides of the second carrier material. The thickness of the second carrier material extends between the first and second surfaces of the second carrier material.

The first air inlet of the first compartment of the cartridge and the second air inlet of the second compartment of the cartridge may each comprise one or more apertures. For example, the first air inlet of the first compartment of the cartridge and the second air inlet of the second compartment of the cartridge may each comprise one, two, three, four, five, six or seven apertures.

The first air inlet of the first compartment of the cartridge and the second air inlet of the second compartment of the cartridge may comprise the same or different numbers of apertures.

As used herein with reference to the invention, the term "nicotine", is used to describe nicotine, nicotine base or a nicotine salt. In embodiments in which the first carrier material is impregnated with nicotine base or a nicotine salt, the amounts of nicotine recited herein are the amount of nicotine base or amount of ionised nicotine, respectively.

The first carrier material may be impregnated with liquid nicotine or a solution of nicotine in an aqueous or non-aqueous solvent.

The first carrier material may be impregnated with natural nicotine or synthetic nicotine.

The first carrier material and the second carrier material may be the same or different.

Advantageously, the first carrier material and the second carrier material have a density of between about 0.1 grams/cubic centimetre and about 0.3 grams/cubic centimetre.

Advantageously, the first carrier material and the second carrier material have a porosity of between about 15 percent and about 55 percent.

The first carrier material and the second carrier material may comprise one or more of glass, cellulose, ceramic, stainless steel, aluminium, polyethylene (PE), polypropylene, polyethylene terephthalate (PET), poly(cyclohexanedimethylene terephthalate) (PCT), polybutylene terephthalate (PBT), polytetrafluoroethylene (PTFE), expanded polytetrafluoroethylene (ePTFE), and BAREX®.

The first carrier material acts as a reservoir for the nicotine.

Advantageously, the first carrier material is chemically inert with respect to nicotine.

Advantageously, the nicotine source comprises the first carrier material impregnated with between about 1 milligram and about 50 milligrams of nicotine.

Preferably, the nicotine source comprises the first carrier material impregnated with between about 3 milligrams and about 30 milligrams of nicotine. More preferably, the nicotine source comprises the first carrier material impregnated with between about 6 milligrams and about milligrams of nicotine. Most preferably, the nicotine source comprises the first carrier material impregnated with between about 8 milligrams and about 18 milligrams of nicotine.

Advantageously, the first compartment of the cartridge may further comprise a flavourant. Suitable flavourants include, but are not limited to, menthol.

Advantageously, the first carrier material may be impregnated with between about 3 milligrams and about 12 milligrams of flavourant.

Preferably, the acid impregnated into the second carrier material is a carboxylic acid. Preferably, the acid is lactic acid.

Advantageously, the acid source comprises the second carrier material impregnated with between about 2 milligrams and about 60 milligrams of lactic acid.

Preferably, the acid source comprises the second carrier material impregnated with between about 5 milligrams and about 50 milligrams of lactic acid. More preferably, the acid source comprises the second carrier material impregnated with between about 8 milligrams and about 40 milligrams of lactic acid. Most preferably, the acid source comprises the second carrier material impregnated with between about 10 milligrams and about 30 milligrams of lactic acid.

The shape and dimensions of the first compartment of the cartridge may be chosen to allow a desired amount of nicotine to be housed in the cartridge.

The shape and dimensions of the second compartment of the cartridge may be chosen to allow a desired amount of acid to be housed in the cartridge.

The first compartment and the second compartment may have substantially the same shape and size.

Advantageously, the cartridge is an elongate cartridge. In embodiments in which the cartridge is an elongate cartridge, the first compartment and the second compartment of the cartridge may be arranged symmetrically about a longitudinal axis of the cartridge.

The cartridge may have any suitable shape. For example, the cartridge may be substantially cylindrical.

The cartridge may have any suitable transverse cross-sectional shape. For example, the transverse cross-sectional shape of the cartridge may be circular, semi-circular, elliptical, triangular, square, rectangular or trapezoidal.

The cartridge may have any suitable size.

For example, the cartridge may have a length of between about 5 millimetres and about millimetres. Advantageously, the cartridge may have a length between about 10 millimetres and about 20 millimetres.

For example, the cartridge may have a width of between about 4 millimetres and about 10 millimetres and a height of between about 4 millimetres and about 10 millimetres. Advantageously, the cartridge may have a width of between about 6 millimetres and about 8 millimetres and a height of between about 6 millimetres and about 8 millimetres.

As used herein with reference to the invention, the terms "proximal", "distal", "upstream" and "downstream" are used to describe the relative positions of components, or portions of components, of the cartridge and aerosol-generating system.

The aerosol-generating system according to the invention comprises a proximal end through which, in use, an aerosol of nicotine salt particles exits the aerosol-generating system for delivery to a user. The proximal end may also be referred to as the mouth end. In use, a user draws on the proximal end of the aerosol-generating system in order to inhale an aerosol generated by the aerosol-generating system. The aerosol-generating system comprises a distal end opposed to the proximal end.

When a user draws on the proximal end of the aerosol-generating system, air is drawn into the aerosol-generating system, passes through the cartridge and exits the aerosol-generating system at the proximal end thereof. Components, or portions of components, of the aerosol-generating system may be described as being upstream or downstream of one another based on their relative positions between the proximal end and the distal end of the aerosol-generating system.

The first air outlet of the first compartment of the cartridge is located at the proximal end of the first compartment of the cartridge. The first air inlet of the first compartment of the cartridge is located upstream of the first air outlet of the first compartment of the cartridge. The second air outlet of the second compartment of the cartridge is located at the proximal end of the second compartment of the cartridge. The second air inlet of the second compartment of the cartridge is located upstream of the second air outlet of the second compartment of the cartridge.

As used herein with reference to the invention, the term "longitudinal" is used to describe the direction between the proximal end and the opposed distal end of the cartridge or aerosol-generating system and the term "transverse" is used to describe the direction perpendicular to the longitudinal direction.

Advantageously, the cartridge comprises a body portion and one or more end caps.

The cartridge may comprise a body portion and a distal end cap.

The cartridge may comprise a body portion and a proximal end cap.

The cartridge may comprise a body portion, a distal end cap and a proximal end cap.

In embodiments in which the cartridge comprises a distal end cap, one or more apertures forming the first air inlet of the first compartment of the cartridge and one or more apertures forming the second air inlet of the second compartment of the cartridge may be provided in the distal end cap.

In embodiments in which the cartridge comprises a proximal end cap, one or more apertures forming the first air outlet of the first compartment of the cartridge and one or more apertures forming the second air outlet of the second compartment of the cartridge may be provided in the proximal end cap.

In embodiments in which the cartridge comprises a cartridge housing, preferably the cartridge housing comprises the body portion and the one or more end caps.

The cartridge housing may be formed from any suitable material or combination of materials. Suitable materials include, but are not limited to, aluminium, polyether ether ketone (PEEK), polyimides, such as Kapton®, polyethylene terephthalate (PET), polyethylene (PE), high-density polyethylene (HDPE), polypropylene (PP), polystyrene (PS), fluorinated ethylene propylene (FEP), polytetrafluoroethylene (PTFE), polyoxymethylene (POM), epoxy resins, polyurethane resins and vinyl resins.

In embodiments in which the cartridge comprises a body portion and one or more end caps, the body portion and the one or more end caps may be formed from the same or different materials.

The cartridge housing may be formed from one or more materials that are nicotine-resistant and acid-resistant.

The first compartment of the cartridge may be coated with one or more nicotine-resistant materials and the second compartment of the cartridge may be coated with one or more acid-resistant materials.

Examples of suitable nicotine-resistant materials and acid-resistant materials include, but are not limited to, polyethylene (PE), polypropylene (PP), polystyrene (PS), fluorinated ethylene propylene (FEP), polytetrafluoroethylene (PTFE), epoxy resins, polyurethane resins, vinyl resins, liquid crystal polymers (LCP) and modified LCPs, such as LCPs with graphite or glass fibres.

Use of one or more nicotine-resistant materials to one or both of form the cartridge housing and coat the interior of the first compartment of the cartridge may advantageously enhance the shelf life of the cartridge.

Use of one or more acid-resistant materials to one or both of form the cartridge housing and coat the interior of the second compartment of the cartridge may advantageously enhance the shelf life of the cartridge.

The cartridge housing may be formed from one or more thermally conductive materials.

The first compartment of the cartridge and the second compartment of the cartridge may be coated with one or more thermally conductive materials.

Use of one or more thermally conductive materials to one or both of form the cartridge housing and coat the interior of the first compartment and the second compartment of the cartridge may advantageously increase heat transfer from a heater to the nicotine source and the lactic acid source.

Suitable thermally conductive materials include, but are not limited to, metals such as, for example, aluminium, chromium, copper, gold, iron, nickel and silver, alloys, such as brass and steel and combinations thereof.

The cartridge housing may be formed of one or more materials having a low resistivity or a high resistivity depending on whether the first compartment and the second compartment are heated by conduction or induction.

The first compartment of the cartridge and the second compartment of the cartridge may be coated with one or more materials having a low resistivity or a high resistivity depending on whether the first compartment and the second compartment are heated by conduction or induction.

The cartridge housing may be formed by any suitable method. Suitable methods include, but are not limited to, deep drawing, injection moulding, blistering, blow forming and extrusion.

The cartridge may be designed to be disposed of once the nicotine in the first compartment and the acid in the second compartment are depleted.

The cartridge may be designed to be refillable.

The cartridge may comprise a cartridge cavity for receiving a heater. Preferably, the cartridge cavity is located between the first compartment and the second compartment. The heater may form part of an aerosol-generating device configured for use with the cartridge.

The cartridge may comprise a heater configured to heat the first compartment and the second compartment. In such embodiments, the heater is advantageously located between the first compartment and the second compartment. In other words, the first compartment and the second compartment are disposed on either side of the heater.

The heater may be an electrical heater. The heater may be a resistive heater.

The heater may comprise a susceptor. During use, an inductive heater is used to inductively heat the susceptor.

Advantageously, the heater is configured to heat the first compartment and the second compartment of the cartridge to a temperature of below about 250 degrees Celsius. Preferably, the heater is configured to heat the first compartment and the second compartment of the cartridge to a temperature of between about 80 degrees Celsius and about 150 degrees Celsius.

Advantageously, the heater is configured to heat the first compartment and the second compartment of the cartridge to substantially the same temperature.

As used herein with reference to the invention, by "substantially the same temperature" it is meant that the difference in temperature between the first compartment and the second compartment of the cartridge measured at corresponding locations relative to the heater is less than about 3 degrees Celsius.

In use, heating the first compartment and the second compartment of the cartridge to a temperature above ambient temperature advantageously enables the vapour concentrations of the nicotine in the first compartment of the cartridge and the vapour pressure of acid in the second compartment of the cartridge to be controlled and balanced proportionally to yield an efficient reaction stoichiometry between the nicotine and the acid. Advantageously, this may improve the efficiency of the formation of nicotine salt particles and the consistency of delivery to a user. Advantageously, it may also reduce the delivery of unreacted nicotine and unreacted acid to a user.

The cartridge may comprise a third compartment downstream of the first compartment and the second compartment and in fluid communication with the first air outlet of the first compartment and the second air outlet of the second compartment. During use, nicotine vapour passing out of the first compartment through the first air outlet may react with acid vapour passing out of the second compartment through the second air outlet in the third compartment to form an aerosol of nicotine salt particles.

The cartridge may comprise a mouthpiece. In embodiments in which the cartridge comprises a cartridge housing, the mouthpiece may be formed integrally with the cartridge housing. The mouthpiece may be formed separately from the cartridge housing. The mouthpiece may be removably attachable to the cartridge housing. The combination of the cartridge housing and the mouthpiece may simulate the shape and dimensions of a combustible smoking article, such as a cigarette, a cigar, or a cigarillo. The combination of the cartridge housing and the mouthpiece may simulate the shape and dimensions of a cigarette.

In embodiments in which the cartridge comprises a third compartment, the mouthpiece may at least partially define the third compartment.

According to a second aspect of the present invention there is provided an aerosol-generating system comprising a cartridge according to the first aspect of the present invention, in accordance with any of the embodiments described herein. The aerosol-generating system further comprises an aerosol-generating device comprising a device housing defining a cavity for receiving at least a portion of the cartridge. The aerosol-generating device also comprises a heater for heating the first compartment and the second compartment of the cartridge.

The aerosol-generating system may comprise a mouthpiece.

The mouthpiece may form part of the cartridge as described herein with respect to the first aspect of the present invention.

The mouthpiece may form part of the aerosol-generating device. Preferably, the mouthpiece is removably attachable to the device housing. The mouthpiece may at least partially define a third compartment as described herein with respect to the first aspect of the present invention.

The mouthpiece may be designed to be disposed of once the nicotine in the first compartment and the acid in the second compartment are depleted.

The mouthpiece may be designed to be reusable. In embodiments in which the mouthpiece is designed to be reusable, the mouthpiece may advantageously be removably attachable to the cartridge or the housing of the aerosol-generating device.

The heater may be an electrical heater. The heater may be a resistive heater.

The heater may be arranged to circumscribe at least a portion of the cartridge when the cartridge is received within the cavity.

The heater may be located within the cavity of the aerosol-generating device and the cartridge may comprise a cartridge cavity for receiving the heater as described herein. In such embodiments, the heater of the aerosol-generating device may advantageously be an elongate heater in the form of a heater blade. The heater blade may have a width that is greater than its thickness. The cartridge cavity may be configured as an elongate slot.

The heater may be an inductive heater and the cartridge may comprise a susceptor for heating the first compartment and the second compartment of the cartridge as described herein.

Preferably, the aerosol-generating system comprises a power supply for supplying power to the heater and a controller configured to control a supply of power from the power supply to the heater.

The power supply may be any suitable power supply, for example a DC voltage source such as a battery. The power supply may be a Lithium-ion battery, a Nickel-metal hydride battery, a Nickel cadmium battery, or a Lithium based battery, for example a Lithium-Cobalt, a Lithium-Iron-Phosphate, Lithium Titanate or a Lithium-Polymer battery.

The power supply may include a rechargeable lithium ion battery. The electrical power supply may comprise another form of charge storage device such as a capacitor. The electrical power supply may require recharging. The electrical power supply may have a capacity that allows for the storage of enough energy for one or more uses of the aerosol-generating device. For example, the electrical power supply may have sufficient capacity to allow for the continuous generation of aerosol for a period of around six minutes, corresponding to the typical time taken to smoke a conventional cigarette, or for a period that is a multiple of six minutes. In another example, the electrical power supply may have sufficient capacity to allow for a predetermined number of puffs or discrete activations.

The controller may be configured to commence a supply of electrical power from the electrical power supply to the heater at the start of a heating cycle. The controller may be configured to terminate a supply of electrical power from the electrical power supply to the heater at the end of a heating cycle.

The controller may be configured to provide a continuous supply of electrical power from the electrical power supply to the heater.

The controller may be configured to provide an intermittent supply of electrical power from the electrical power supply to the heater. The controller may be configured to provide a pulsed supply of electrical power from the electrical power supply to the heater. A pulsed supply of electrical power to the heater may facilitate control of the total output from the heater during a time period. Controlling a total output from the heater during a time period may facilitate control of temperature.

The controller may be configured to vary the supply of electrical power from the electrical power supply to the heater. The controller may be configured to vary a duty cycle of the pulsed supply of electrical power. The controller may be configured to vary at least one of a pulse width and a period of the duty cycle.

The aerosol-generating device may comprise one or more temperature sensors arranged to sense the temperature of at least one of the heater, the first compartment and the second compartment of the cartridge. The controller may be configured to control a supply of power to the heater based on the sensed temperature.

The aerosol-generating device may comprise a user input device. The user input device may comprise at least one of a push-button, a scroll-wheel, a touch-button, a touch-screen, and a microphone. The user input device may allow a user to control one or more aspects of the operation of the aerosol-generating device. The user input device may allow a user to activate a supply of electrical power to the heater, to deactivate a supply of electrical power to the heater, or both.

For the avoidance of doubt, features described above in relation to one aspect of the invention may also be applicable to other aspects of the invention. In particular, features described above in relation to the cartridge of the invention may also relate, where appropriate, to the aerosol-generating systems of the invention, and vice versa.

Embodiments of the invention will now be described, by way of example only, with reference to the accompanying drawings, in which.

Figure 1:
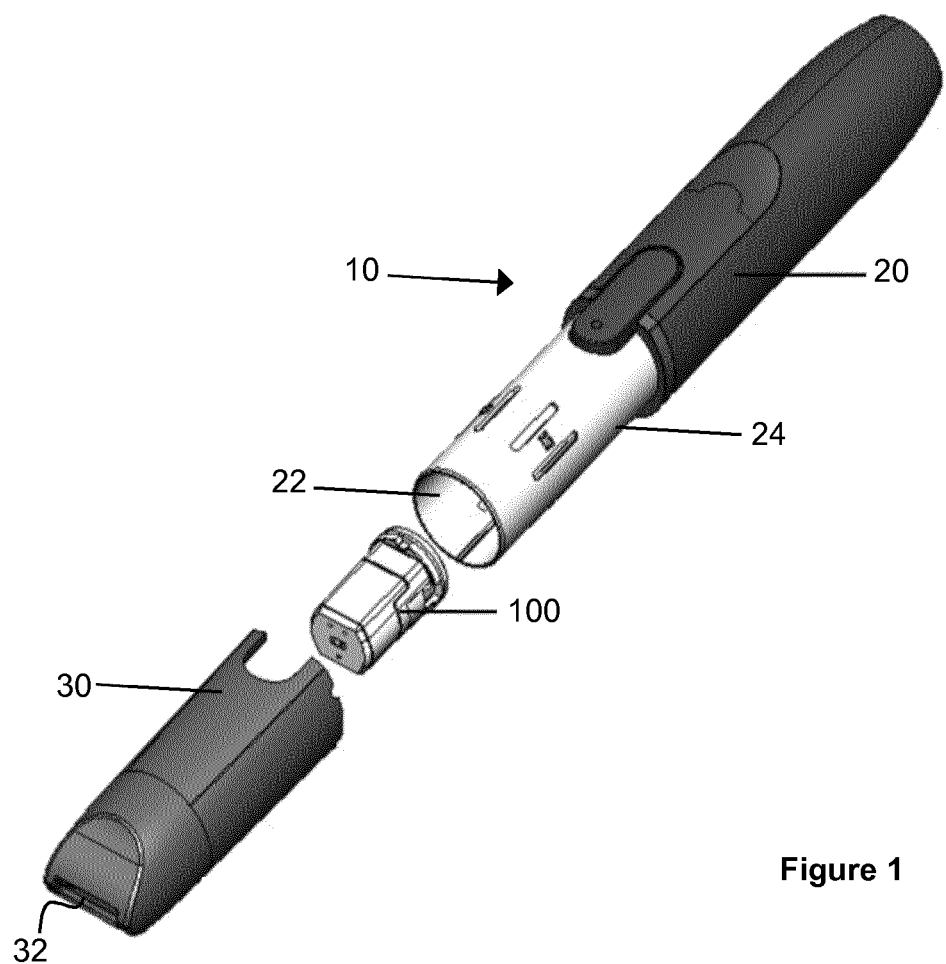
FIG. 1 is an exploded perspective view of an aerosol-generating system according to an embodiment of the present invention.
Figure 2:
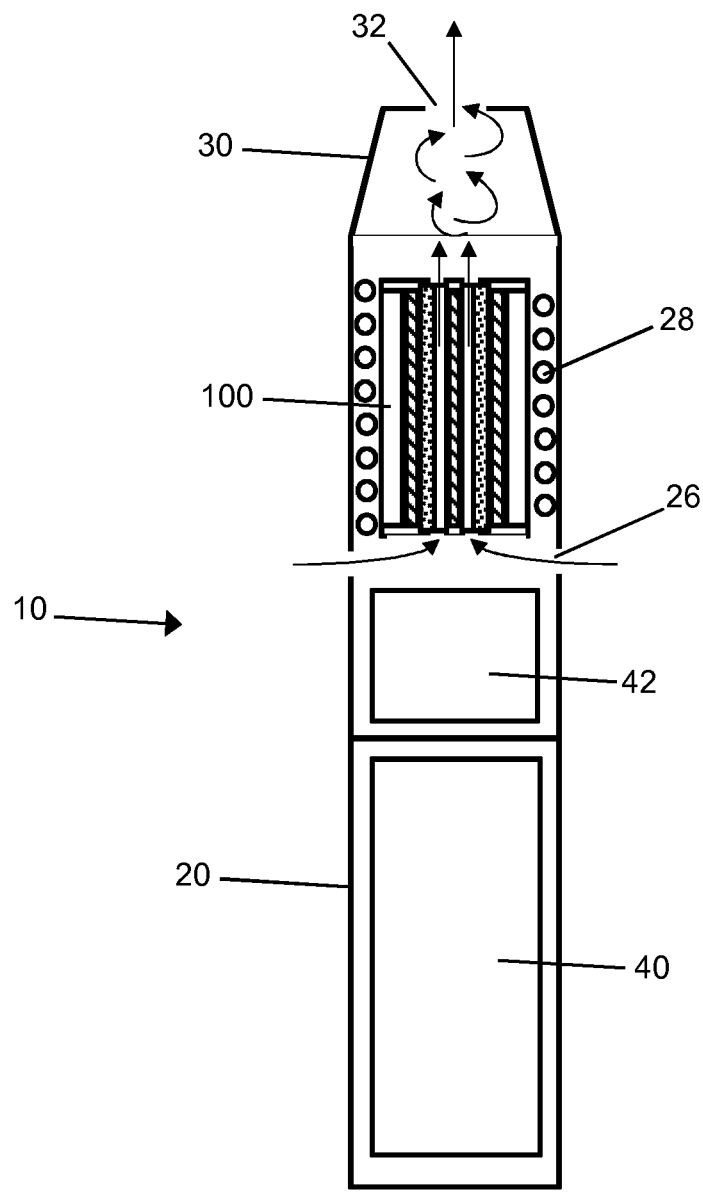
FIG. 2 is a cross-sectional view of the aerosol-generating system of FIG. 1.

FIGS. 1 and 2 show an aerosol-generating system 10 comprising an aerosol-generating device 20 and a cartridge 100 for use with the aerosol-generating device 20. The aerosol-generating system further comprises a mouthpiece 30 configured to attach releasably to a proximal end 24 of the aerosol-generating device 20.

The aerosol-generating device 20 comprises a housing defining a cavity 22 for receiving the cartridge 100 through an opening at the proximal end 24 of the aerosol-generating device 20. The aerosol-generating device 20 comprises a heater in the form of an inductor coil 28 within the cavity 22. The inductor coil is held against the internal walls the cavity 22 as shown in FIG. 2. The aerosol-generating device 20 comprises an electrical energy supply 40 in the housing, in this example a rechargeable lithium ion battery. The device 10 further comprises a controller 42 connected to the electrical energy supply 40, the inductor coil 28 and a user interface (not shown). In this embodiment, the user interface comprises a mechanical button. Upon activating the user interface, the controller 42 supplies the inductor coil 28 with a high frequency oscillating electrical current to produce an oscillating magnetic field. As further described herein, the oscillating magnetic field heats one or more susceptors in the cartridge 100 as a result of induced eddy currents and hysteresis losses in the one or more susceptors. Inductively heating the susceptors heats a nicotine source and an acid source contained within the cartridge 100, producing a nicotine vapour and an acid vapour. As a user puffs on the mouthpiece 30, a flow of air is drawn from a device air inlet 26 through the cartridge 100 to convey the vaporized nicotine and acid towards the mouthpiece 30. The vaporized nicotine and acid, each in a gas phase, react and cool in the mouthpiece 30 to form an aerosol containing nicotine salt particles. During the puff, the user receives a volume of the aerosol through a mouthpiece air outlet 32.

Figure 3:
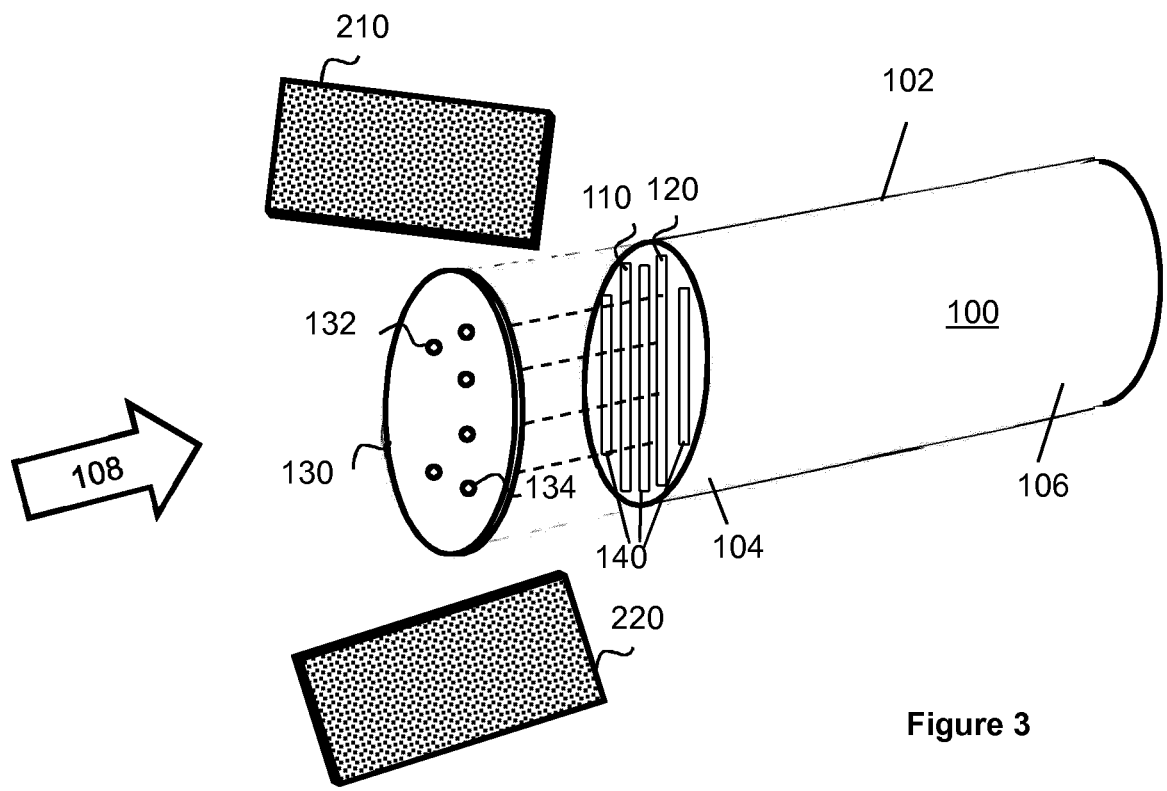
FIG. 3 is an exploded perspective view of the cartridge of FIG. 1.

FIG. 3 is an exploded view of the cartridge 100. The cartridge 100 has a length of about millimetres, a width of about 7.1 millimetres and a height of about 6.75 millimetres. The cartridge 100 in this illustrated example comprises an elongate cartridge body 102 closed by end caps 130, 131 at its distal end 104 and its proximal end 106. The body 102 and the end caps 130, 131 together form a cartridge housing. The body 102 has a length of about 11 millimetres, a width of about 7.1 millimetres and a height of about 6.75 millimetres. Each end cap 130, 131 has a length of about 2 millimetres, a width of about 7.1 millimetres and a height of about 6.75 millimetres. The cartridge 100 comprises a nicotine source 210 contained in a first compartment 110 and an acid source 220 contained in a second compartment 120 of the cartridge 100. In this embodiment the acid source 220 is a lactic acid source. The first compartment 110 and the second compartment 120 each extend longitudinally within the cartridge body 102. The first compartment 110 and the second compartment 120 are arranged to be closed by the end caps 130, 131 at their respective distal end 104 and proximal end 106. The first compartment 110 and the second compartment 120 are identical compartments each having a substantially rectangular cross-section with a depth of about 1 millimetres.

The first compartment 110 and the second compartment 120 are arranged in a parallel configuration. The incoming air stream splits before entering the first compartment 110 and the second compartment 120. The nicotine vapour and the lactic acid vapour are generated simultaneously in the separate compartments 110, 120.

The distal end cap 130 comprises a plurality of air inlets 132, 134 providing flow passages between an incoming air flow 108 and the first and second compartments 110, 120. The air inlets are identical apertures through the distal end cap 130. The plurality of air inlets 132, 134 comprise first air inlets 132 in fluid communication with the first compartment 110, and second air inlets 134 in fluid communication with the second compartment 120. In the illustrated example, there are more second air inlets 134 than first air inlets 132, which results in a larger total cross-sectional flow area through the second air inlets 134 than through the first air inlets 132. The larger total cross-sectional flow area through the second air inlets 134 enables a higher volumetric air flow through the second compartment 120 than the first compartment 110. The higher volumetric air flow through the second compartment 120 causes more acid to vaporise in the second compartment 120 than would be the case if there were fewer second air inlets 134.

The proximal end cap 131 comprises air outlets 133, 135 that mirror the air inlets 132,134 at the distal end cap 130. The air outlets 133, 135 at the proximal end cap 131 are in fluid communication with the first and second compartments 110, 120, as well as the mouthpiece air outlet 32 at the mouthpiece 30. The first compartment 110 and the second compartment 120 each extend from the distal end cap 130 to the proximal end cap 131. In other words, the first compartment 110 and the second compartment 120 both extend all the way along the length of the cartridge body 102.

The cartridge body 102 comprises a plurality of heater cavities 140 each extending along the longitudinal axis of the cartridge 100. Each of the heater cavities has a depth of 0.4 millimetres. The heater cavities 140 are parallel to the first compartment 110 and the second compartment 120. Each of the heater cavities 140 and its corresponding first compartment 110 or second compartment 120 are separated by 0.4 millimetres. Each of the plurality of heater cavities 140 contains a susceptor 141. The plurality of heater cavities 140 are closed at both the distal end 104 and the proximal end 106 by the distal end cap 130 and proximal end cap 131. In the illustrated example, each of the first compartment 110 and the second compartment 120 is sandwiched between a pair of heater cavities 140. In this embodiment, a plurality of identical susceptors 141 are used, one placed in each heater cavity 140. During use both the nicotine source 210 and the acid source 220 are heated to the same temperature by inductive heating of the susceptors 141.

The nicotine source 210 comprises a first carrier material 211 located in the first compartment 110 and impregnated with nicotine. In this example, the first carrier material 211 comprises a porous ceramic substrate impregnated with a nicotine liquid. The nicotine liquid also comprises flavourings that vaporise with the nicotine when the nicotine source 210 is heated. The flavourings may produce a desirable taste in the generated aerosol. In this example, the first carrier material 211 comprises a porous ceramic substrate impregnated with about 10 milligrams of nicotine and about 4 milligrams of menthol.

The first carrier material 211 comprises a first surface 213 and a second surface 215 opposite the first surface 213. A first airflow path 217 through the first compartment 110 extends across the first surface 213 of the first carrier material 211.

The acid source 220 comprises a second carrier material 221 located in the second compartment 120 and impregnated with lactic acid. In this example, the second carrier material 221 comprises a porous ceramic substrate impregnated with about 20 milligrams of lactic acid.

The second carrier material 221 comprises a first surface 223 and a second surface 225 opposite the first surface 223. A second airflow path 227 through the second compartment 120 extends across the first surface 223 of the second carrier material 221.

Figure 4:
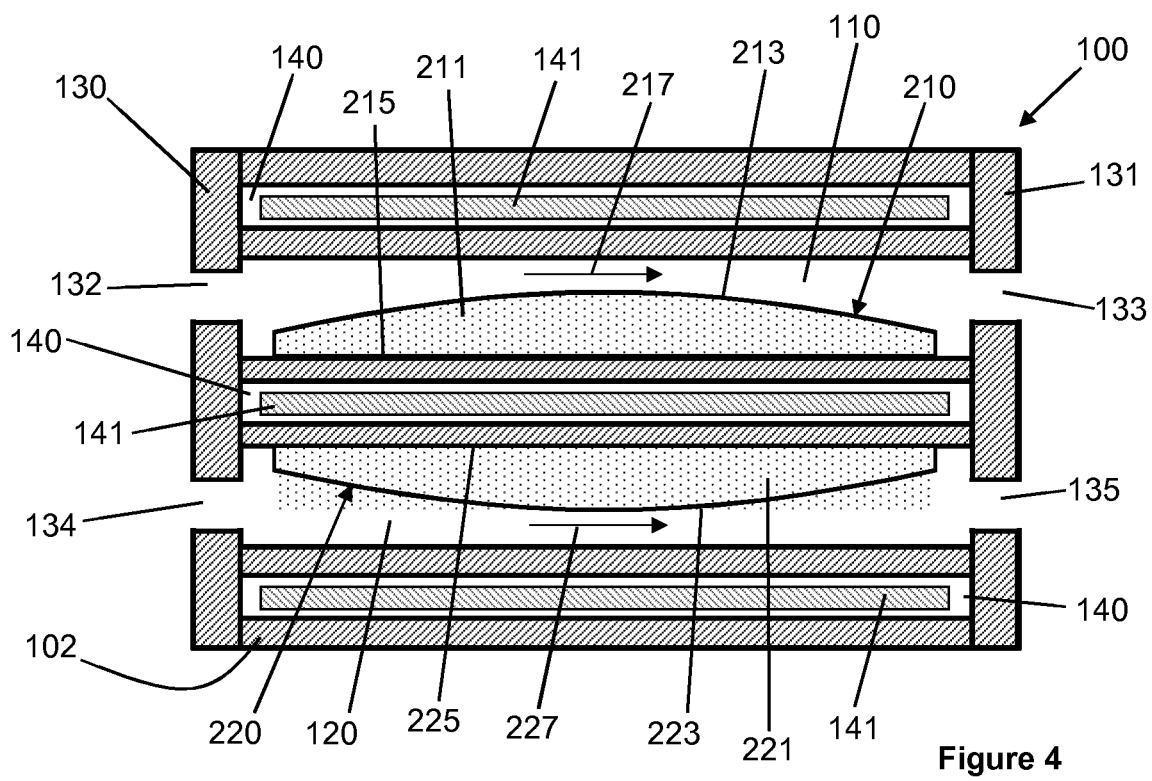
FIG. 4 is a cross-sectional view of the cartridge of FIG. 3.

As shown in FIG. 4, each of the first carrier material 211 and the second carrier material 221 has a thickness that varies in a direction along the first airflow path 217 and the second airflow path 227 respectively. In the embodiment shown in FIG. 4, the varying thickness of the first and second carrier materials 211, 221 is achieved by providing each of the first surface 213 of the first carrier material 211 and the first surface 223 of the second carrier material 221 with a convex shape.

Figure 5:
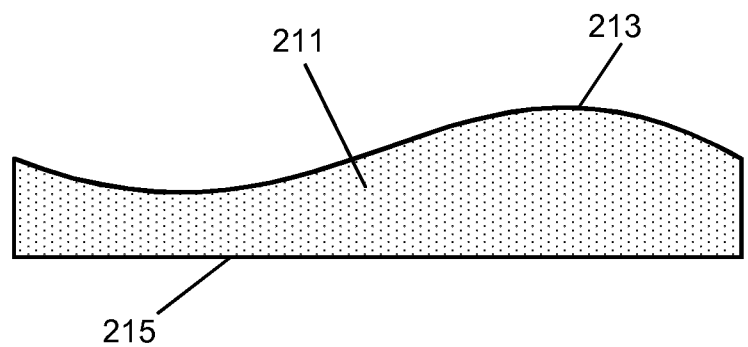
FIGS. 5 to 10 illustrate alternative configurations for the carrier materials of the cartridge of FIG. 4.

FIG. 5 shows an alternative shape for the first carrier material 211 in which the varying thickness of the first carrier material 211 is achieved by providing the first surface 213 of the first carrier material 211 with an undulating shape. It will be appreciated that the same shape may be applied to the first surface 223 of the second carrier material 221.

Figure 6:
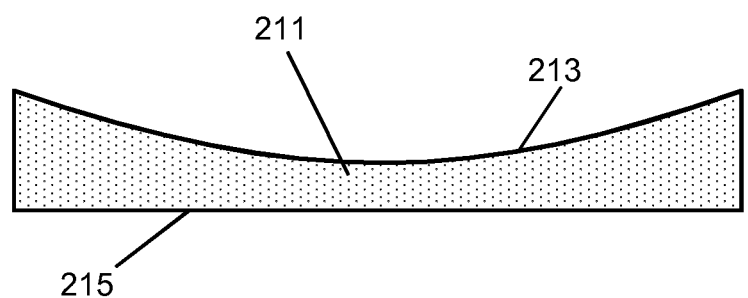

FIG. 6 shows an alternative shape for the first carrier material 211 in which the varying thickness of the first carrier material 211 is achieved by providing the first surface 213 of the first carrier material 211 with a concave shape. It will be appreciated that the same shape may be applied to the first surface 223 of the second carrier material 221.

Figure 7:
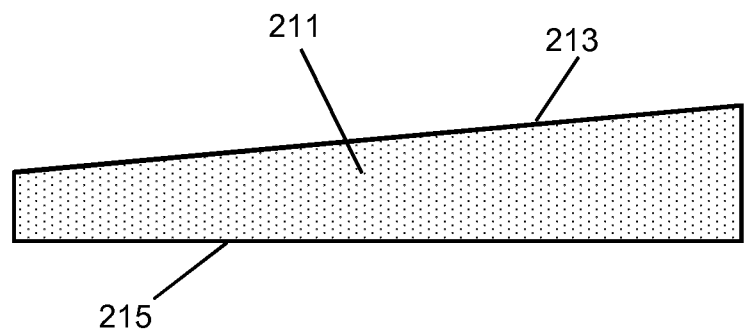

FIG. 7 shows an alternative shape for the first carrier material 211 in which the varying thickness of the first carrier material 211 is achieved by inclining the first surface 213 of the first carrier material 211 with respect to the second surface 215 of the first carrier material 211 so that the first carrier material 211 has a tapered shape. It will be appreciated that the same shape may be applied to the second carrier material 221.

Figure 8:
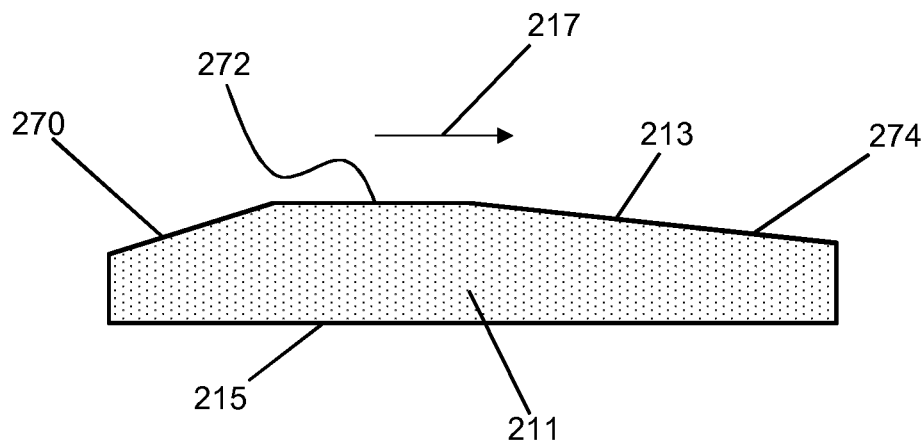

FIG. 8 shows an alternative shape for the first carrier material 211 in which the varying thickness of the first carrier material 211 is achieved by providing the first surface 213 with a multifaceted shape. In particular, the first surface 213 has an inclined portion 270, a flat portion 272, and a declined portion 274. In the example shown in FIG. 9, the inclined portion 270 is shorter than the declined portion 274 so that the first surface 213 has an asymmetrical shape. It will be appreciated that the same shape may be applied to the second carrier material 221.

Figure 9:
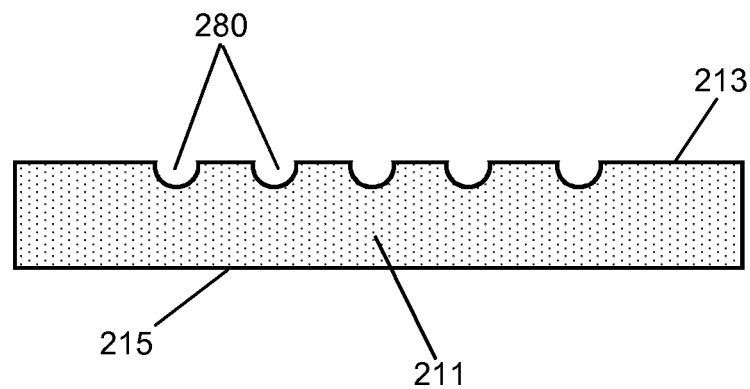

FIG. 9 shows an alternative shape for the first carrier material 211 in which the varying thickness of the first carrier material 211 is achieved by providing the first surface 213 with a plurality of depressions 280 each having a hemispherical shape. It will be appreciated that the same shape may be applied to the second carrier material 221.

Figure 10:
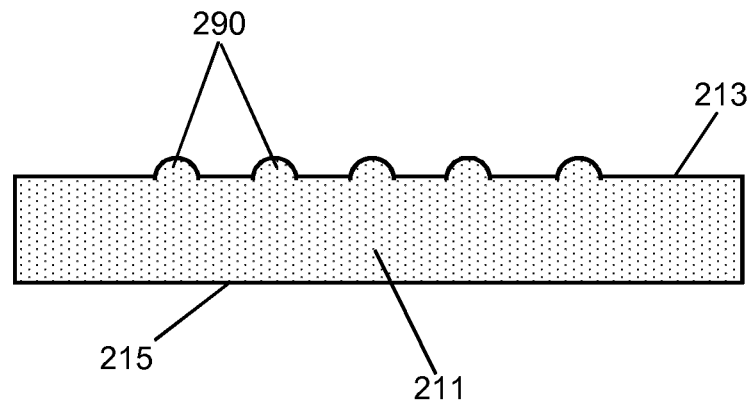

FIG. 10 shows an alternative shape for the first carrier material 211 in which the varying thickness of the first carrier material 211 is achieved by providing the first surface 213 with a plurality of protrusions 290 each having a hemispherical shape. It will be appreciated that the same shape may be applied to the second carrier material 221.

The invention claimed is:

1. A cartridge for use in an aerosol-generating system for the generation of an aerosol comprising nicotine salt particles, the cartridge comprising:
   a first compartment containing a nicotine source comprising a first carrier material impregnated with nicotine, the first compartment having a first air inlet and a first air outlet, the first compartment defining a first airflow path extending across a first surface of the first carrier material between the first air inlet and the first air outlet; and
   a second compartment containing an acid source comprising a second carrier material impregnated with an acid, the second compartment having a second air inlet and a second air outlet, the second compartment defining a second airflow path extending across a first surface of the second carrier material between the second air inlet and the second air outlet;
   wherein the first compartment and the second compartment are arranged in parallel within the cartridge; and
   wherein a thickness of at least one of the first carrier material and the second carrier material varies in a direction along the first airflow path or the second airflow path respectively.

2. The cartridge according to claim 1, wherein a thickness of the first carrier material varies in a direction along the first airflow path and wherein a thickness of the second carrier material varies in a direction along the second airflow path.

3. The cartridge according to claim 1, wherein at least a portion of the first surface of the first carrier material has a non-planar shape.

4. The cartridge according to claim 3, wherein at least a portion of the first surface of the first carrier material has at least one of a convex shape, a concave shape, an undulating shape, a multifaceted shape, one or more depressions, and one or more protrusions.

5. The cartridge according to claim 1, wherein at least a portion of the first surface of the second carrier material has a non-planar shape.

6. The cartridge according to claim 5, wherein at least a portion of the first surface of the second carrier material has at least one of a convex shape, a concave shape, an undulating shape, a multifaceted shape, one or more depressions, and one or more protrusions.

7. The cartridge according to claim 1, further comprising a cartridge housing defining the first compartment and the second compartment, wherein the first carrier material is secured to the cartridge housing at a second surface of the first carrier material, and wherein the second carrier material is secured to the cartridge housing at a second surface of the second carrier material.

8. The cartridge according to claim 7, wherein the second surface of the first carrier material is opposite the first surface of the first carrier material, and wherein the second surface of the second carrier material is opposite the first surface of the second carrier material.

9. The cartridge according to claim 1, wherein the first compartment and the second compartment have substantially the same shape and size.

10. The cartridge according to claim 1, wherein the acid is a carboxylic acid.

11. The cartridge according to claim 10, wherein the acid is lactic acid.

12. The cartridge according to claim 1, wherein the nicotine source comprises the first carrier material impregnated with between 1 milligram and about 50 milligrams of nicotine.

13. The cartridge according to claim 1 wherein the acid source comprises the second carrier material impregnated with between 2 milligrams and about 60 milligrams of lactic acid.

14. An aerosol-generating system comprising:
the cartridge according to claim 1; and
an aerosol-generating device comprising:
a device housing defining a cavity for receiving at least a portion of the cartridge; and
a heater for heating the first compartment and the second compartment of the cartridge.

15. The aerosol-generating system according to claim 14, wherein the cartridge comprises a susceptor located between the first compartment and the second compartment and the heater comprises an inductive heater surrounding at least a portion of the cavity of the aerosol-generating device.

* * * * *